United States Patent
Breining et al.

[11] Patent Number: 5,827,272
[45] Date of Patent: Oct. 27, 1998

[54] SIMPLIFIED TORQUING ELECTRODE CATHETER

[75] Inventors: Peter M. Breining, Palo Alto; Scott H. West, Tracy, both of Calif.

[73] Assignee: Medtronic CardioRhythm, San Jose, Calif.

[21] Appl. No.: 511,823

[22] Filed: Aug. 7, 1995

[51] Int. Cl.⁶ ............................................ A61N 1/00
[52] U.S. Cl. ........................ 606/41; 607/119; 600/585
[58] Field of Search ............................ 606/41; 607/119, 607/122, 127, 125, 128; 604/95, 105, 280, 264; 128/642, 772; 600/374, 377, 585

[56] References Cited

U.S. PATENT DOCUMENTS

| | | |
|---|---|---|
| Re. 34,502 | 1/1994 | Webster, Jr. . |
| 4,301,790 | 11/1981 | Bol et al. ............................... 128/642 |
| 5,125,896 | 6/1992 | Hojeibane . |
| 5,185,004 | 2/1993 | Lashinski . |
| 5,231,995 | 8/1993 | Desai . |
| 5,242,441 | 9/1993 | Avitall . |
| 5,282,845 | 2/1994 | Bush et al. ............................ 607/128 |
| 5,315,996 | 5/1994 | Lundquist . |
| 5,318,041 | 6/1994 | DuBois et al. . |
| 5,318,525 | 6/1994 | West et al. . |
| 5,318,528 | 6/1994 | Heaven et al. . |

*Primary Examiner*—John P. Lacyk
*Assistant Examiner*—Stephen Huang
*Attorney, Agent, or Firm*—Townsend and Townsend and Crew LLP

[57] ABSTRACT

An electrode catheter (2) includes a handle (4) to which a catheter shaft (6) is mounted. The catheter shaft has a distal end (10) carrying plurality of electrodes (12). Dual purpose wires (18) extend from an electrical connector (14) on the handle, through separate axial lumens (16) in the catheter shaft and to the electrodes. The dual purpose wires are physically secured at their distal and proximal ends to the distal end of the catheter shaft and to the handle, respectively, so that rotation of the handle causes a rotational torque to be transmitted through the dual purpose wires to the distal end of the catheter shaft. Each dual purpose wire has an electrical resistance of no greater than about 0.80 ohms per centimeter and a torsional stiffness of at least about 0.25 to 1.0 inch-ounce (17654 to 70616 dyne-cm) for each 110 cm length of catheter shaft when the proximal end of the catheter shaft is rotated 3 turns. This construction provides a simply constructed, low cost torquing electrode catheter.

24 Claims, 1 Drawing Sheet

SIMPLIFIED TORQUING ELECTRODE CATHETER

BACKGROUND OF THE INVENTION

A catheter is a flexible, tubular device used for various diagnostic and therapeutic purposes. To permit the catheter to be guided along a path within the body, the tip of the catheter can be bent into a curve, typically through pulling on a manipulator wire passing through a lumen within the catheter. This is commonly termed axial deflection. Rotation of the curved, axially deflected tip about the longitudinal axis of the catheter causes the tip to move along an accurate path. This is commonly termed lateral deflection. As an alternative to the active deflection described above, the catheter tip can be pre-formed to a desired shape.

One way to rotate the tip of the catheter is to rotate the handle or connector of the catheter which transmits a torque along the catheter shaft to the tip. The catheter shaft is made of a relatively soft polymeric material which flexes easily. Therefore, to effectively transmit torque along the catheter shaft by rotating the handle, the catheter shaft needs torsional stiffness greater than that available with conventional polymeric materials from which the outer shaft is typically made. To provide the desired torsional stiffness, the outer shaft is typically made to incorporate a wire braid or other torsional stiffeners into the outer shaft. The wire braid does not increase the bending stiffness very much, but does provide a substantial increase in torsional stiffness.

A second way to rotate the tip of the catheter is to use a core wire passing through a lumen within the catheter shaft. The core wire has a relatively high torsional stiffness and is secured to the tip of the catheter so that rotating the core wire at the handle causes torque to be exerted along the core wire (not along the catheter shaft) to the tip of the catheter, thus causing the curved catheter tip to be deflected laterally.

SUMMARY OF THE INVENTION

The present invention is directed to an electrode catheter which uses dual purpose wires to eliminate the need for a braided catheter shaft to provide the necessary torque transmission from the handle or connector to the distal end of the catheter shaft. The invention does so in a simplified way by using wires with relatively high torsional stiffness to act as both the electrical conductors between the electrodes and the handle/connector and to transmit torque from the handle/connector to the distal end of the catheter shaft. The invention permits a torquing electrode catheter to be made more simply than conventional torquing electrode catheters, thus lowering cost.

The electrode catheter includes a handle/connector to which a proximal end of the catheter shaft is mounted. The catheter shaft has a distal end to which a plurality of electrodes are mounted. A number of dual purpose wires extend along the catheter shaft from the handle/connector to the distal end of the catheter shaft. Each electrode is electrically connected to one of the dual purpose wires. The dual purpose wires are physically secured at their distal and proximal ends to the distal end of the catheter shaft and to the handle/connector, respectively, so that rotation of the handle/connector causes a rotational torque to be transmitted through the dual purpose wires to the distal end of the catheter shaft. Each dual purpose wire preferably has an electrical resistance of no greater than about 0.80 ohms per centimeter. This construction provides a simply constructed, low cost torquing electrode catheter.

The mechanical connection of the dual purpose wires to the handle/connector and to the distal end of the catheter shaft is preferably through the connection of the dual purpose wire to the electrical connector of the handle/connector and to the electrodes at the distal end of the catheter shaft. In some situations it may be desired to provide additional mechanical coupling between one or more of the dual purpose wires and the distal end of the catheter shaft or the handle/connector, or both, instead of relying only on the connection to the electrodes and electrical connector to transmit the torquing force.

Preferably, each dual purpose wire passes through a separate axial lumen within the catheter shaft. However, separate axial lumens are not necessarily required for each dual purpose wire.

Other features and advantages will appear from the following description in which the preferred embodiments have been set forth in detail in conjunction with the accompanying drawings.

DESCRIPTION OF THE PREFERRED EMBODIMENTS

Figure 1:
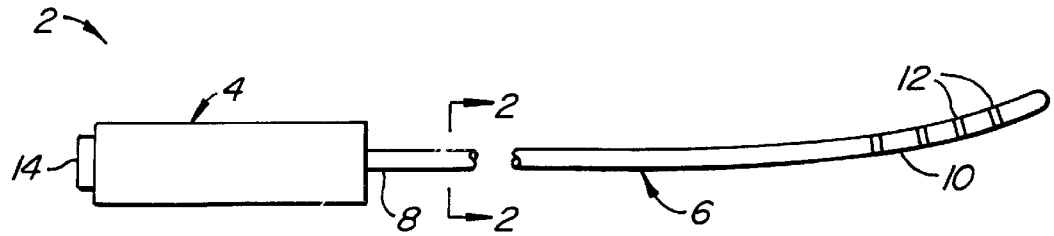
FIG. 1 is a simplified overall view showing an electrode catheter made according to the invention.
Figure 2:
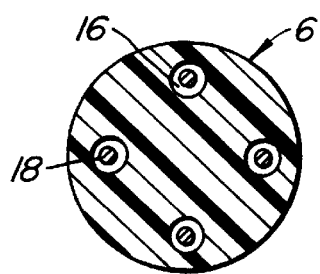
FIG. 2 is a radial cross-sectional view taken along line 2—2 of FIG. 1.
Figure 3:
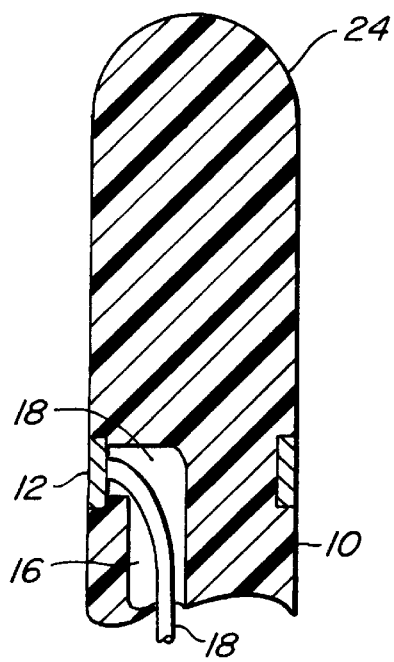
FIG. 3 is an axial cross-sectional view of the distal end of the catheter shaft of FIG. 1.

FIGS. 1–3 illustrate a torquing electrode catheter 2 made according to the invention. Catheter 2 includes broadly a handle 4 and a catheter shaft 6. Catheter shaft 6 has a proximal end 8 fixed to handle 4 and a distal end 10. Distal end 10 has a number of band electrodes 12 connected thereto while handle 4 has an electrical connector 14 at its proximal end.

FIGS. 2 and 3 illustrate that catheter shaft 6, made of a polyamide polyether block copolymer, such as that sold under the trademark Pebax, has four axial bores 16 formed along its length. The distal ends 17 of each axial bore 16 opens onto one of the band electrodes 12. See FIG. 3. This permits a dual purpose wire 18 to be secured to an individual band electrode 12 at one end and to electrical connector 14 at the other end. Wires 18 are preferably 0.005 to 0.16 inch (0.13 to 0.41 mm), and more preferably about 0.013 inch (0.33 mm), diameter metal wires of MP35N and may have a PTFE coating. Each dual purpose wire 18 has an electrical resistivity of about 0.11 to 0.80 ohm per centimeter of length. Therefore, wire 18 will exhibit a resistance of about 7 to 52 ohms for a 65 cm (pediatric) length, about 9 to 64 ohms for an 80 cm (standard) length and about 12 to 88 ohms for a 110 cm (long) length. Resistances of about 10–15 ohms should be sufficiently low for ablation. In one preferred embodiment electrodes 12 and wires 18 are sized for both mapping and other such lower-power functions as well as for ablation. In some cases heavier duty wire may be needed to handle increased energy transmission for ablation procedures. Typically 2 to 10 dual purpose wires 18 (for 2 to 10 electrodes 12) would be used with catheter 2. The fewer the number of wires 18, the greater the diameter each wire must be to provide the same total cross-sectional area for all wires 18 in a catheter 2.

Figure 1A:
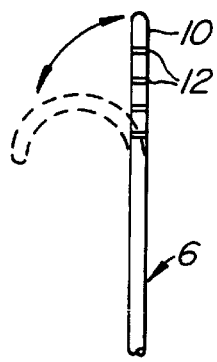
FIGS. 1A and 1B are simplified views of the distal end of the catheter shaft of FIG. 1 illustrating axial and lateral deflection, respectively.

Distal end 10 can be pre-bent into a desired permanent shape prior to use. Alternatively, one (or more) of the dual purpose wires 18 can also serve as a manipulator wire 20, see FIG. 4, for use along catheter shaft 6 coupling distal end 10 to an appropriate manipulator actuator on the handle, not shown. Pulling on manipulator wire 20 would cause distal end 10 to bend, that is, deflect axially, in the amount desired. See FIG. 1A. In either event, that is whether catheter shaft 6 has its distal end pre-bent or is deflected using dual purpose/manipulation wire 20, it is desired to place dual purpose wires 18 under a small amount of tension (so that shaft 6 is in compression) when manufacturing catheter 2. Providing dual purpose wires 18 with about a 1% tension over their lengths permits the lateral deflection of the bent distal end 10 of catheter shaft 6, see FIG. 1B, without an annoying radial oscillation of the catheter tip as could occur if wires 18 were not so initially tensioned. Also, it is desirable to heat and reform the very tip 24 of catheter 2 (beyond distal band electrode 12) into a rounded shape as shown in FIG. 3. This obviates the need for a rounded metal electrode; eliminating this costly machined part reduces the catheter cost significantly.

Figure 4:
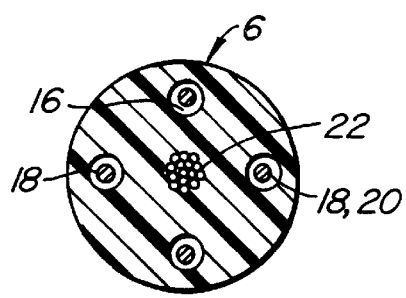
FIG. 4 is a cross-sectional view of an alternative embodiment of the invention similar to that of FIG. 2 showing a damping core and a manipulator wire.

The alternative embodiment of FIG. 4 also shows use of a damping core 22 made of synthetic polyester fibers and sold under the trademark Dacron. Damping core 22 has a diameter of about 0.015 inch (0.38 mm) and is composed of approximately 200 strands. Damping core 22 is co-extruded with catheter shaft 6 and helps to dampen vibrations and other movement of catheter shaft 6. Damping core 22 could have a braided, spiral wrapped or straight bundle configuration and be made of other polymers or metallic fibers (or a combination).

The selection of dual purpose wires 18 depends upon several factors including the required electrical current carrying capacity, resistivity, bending stiffness, torsional stiffness and maximum allowable diameter. The primary criteria are a maximum electrical resistivity of preferably no more than about 0.80 ohm per centimeter in length, and a minimum torsional stiffness. The preferred minimum torsional stiffness is to some extent dependent on the number of dual purpose wires 18; that is, a catheter with 10 dual purpose wires 18 may not need to have each wire be as stiff as a catheter with 2 dual purpose wires. Torque transmission for a catheter 2 having a length of about 110 cm is preferably in the range of 0.25 to 1.0 inch-ounce (17654 to 70616 dyne-cm), and more preferably about 0.4 inch-ounce (28246 dyne-cm), when proximal end 8 of catheter shaft 6 is rotated about 3 turns.

Figure 1B:
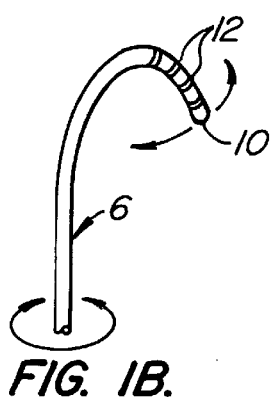

Electrode catheter 2 is especially useful for electrophysiological procedures, such as mapping. In the preferred embodiment, all of the electrodes are band electrodes 12. If desired, a tip electrode or electrodes which do not extend entirely around catheter shaft 6 could be used. The lateral deflection of distal end 10 is achieved by rotating handle 4 which transmits the torque to distal end 10 primarily through the relatively stiff dual purpose wires 18. This permits lateral deflection, as shown in FIG. 1B, to be achieved in a simple manner. Other conventional structures, such as radiopaque markers, can be used to aid the proper deflection and positioning of distal end 10. It may be desired to form distal end 10 of shaft 6 into a desired curve, typically by heating and reforming the final several cm of the distal end 10 to achieve a variety of shapes. Some or all of the dual purpose wires 18 can be tapered, or otherwise provided with a variable diameter, to provide variable stiffness for catheter 2.

Other modifications and variation can be made to the disclosed embodiments without departing from the subject of the invention as defined in the following claims.

What is claimed is:

1. An electrode catheter comprising:

a handle;

a catheter shaft having an axial lumen, a proximal end and a distal end, the proximal end mounted to the handle;

a plurality of electrodes mounted to the distal end;

a dual purpose wire secured to each of said electrodes in an electrically-conductive manner, each said dual purpose wire having an electrical resistance of no greater than about 0.80 ohm per cm to provide sufficient electrical current carrying capacity and resistivity for an electrophysiology procedure;

said dual purpose wires secured to and extending from the handle, extending through the axial lumen in said catheter shaft and to said electrodes so to act as electrical conductors electrically coupling the handle and the electrodes and to transmit torque from said handle along said dual purpose wires to said distal end of the catheter shaft; and said catheter shaft and dual purpose wires together having a torsional stiffness of about 0.25 to 1.0 inch-ounce per 110 cm of length when the proximal end of the catheter shaft is rotated about 3 turns to provide a torsional stiffness sufficient to laterally deflect the distal end of the shaft by rotating the proximal end of the shaft.

2. A catheter according to claim 1 wherein the handle comprises an electrical connector to which the dual purpose wires are secured.

3. A catheter according to claim 1 wherein at least some of said electrodes are band electrodes circumscribing said catheter shaft.

4. A catheter according to claim 1 wherein said catheter shaft includes a plurality of said axial lumens.

5. A catheter according to claim 4 wherein each said dual purpose wire is housed within a separate one of said axial lumens.

6. A catheter according to claim 1 wherein said dual purpose wires are made of metal.

7. A catheter according to claim 6 wherein the dual purpose wires have diameters of 0.005 to 0.16 inch.

8. A catheter according to claim 1 wherein said dual purpose wires are coated with a low-friction material.

9. A catheter according to claim 8 wherein said catheter shaft is made of a polyamide polyether block copolymer.

10. A catheter according to claim 1 wherein said catheter shaft is made of a homogeneous material.

11. A catheter according to claim 1 wherein said distal end of the catheter shaft is preformed with a desired shape.

12. The catheter according to claim 11 wherein the distal end has a centerline and the preformed distal end defines a curved centerline.

13. The catheter according to claim 11 wherein the distal end comprises a tip and the preformed distal end comprises a rounded tip.

14. A catheter according to claim 1 wherein at least one of said dual purpose wires has a variable diameter to provide a variable stiffness for the catheter.

15. A catheter according to claim 1 wherein each said dual purpose wire has an electrical resistance of about 0.11 to 0.80 ohm per cm.

16. A simplified torquing electrode catheter comprising:

a handle comprising an electrical connector;

a catheter shaft having a plurality of axial lumens, a proximal end and a distal end, the proximal end mounted to the handle;

said catheter shaft being made of a homogeneous material;

a plurality of electrodes mounted to the distal end;

a dual purpose wire secured to each of said electrodes in an electrically-conductive manner, each said dual purpose wire having an electrical resistance of no greater than about 0.80 ohms per cm to provide sufficient electrical current carrying capacity and resistivity for an electrophysiology procedure;

each of said dual purpose wires secured to and extending from the handle, extending through a separate one of said axial lumens and to said electrodes so to act as electrical conductors electrically coupling the handle and the electrodes and to transmit torque from said handle along said dual purpose wires to said distal end of the catheter shaft; and said catheter shaft and dual purpose wires together having a torsional stiffness of about 0.25 to 1.0 inch-ounce per 110 cm of length when the proximal end of the catheter shaft is rotated about 3 turns to provide a torsional stiffness sufficient to laterally deflect the distal end of the shaft by rotating the proximal end of the shaft.

17. A catheter according to claim 16 wherein said dual purpose wires have diameters of about 0.005 to 0.16 inch.

18. An electrode catheter comprising:

a handle;

a catheter shaft having an axial lumen, a proximal end and a distal end, the proximal end mounted to the handle;

a plurality of electrodes mounted to the distal end;

a dual purpose wire secured to each of said electrodes in an electrically-conductive manner, each said dual purpose wire having an electrical resistance of no greater than about 0.80 ohm per cm;

said dual purpose wires secured to and extending from the handle, extending through the axial lumen in said catheter shaft and to said electrodes so to act as electrical conductors electrically coupling the handle and the electrodes and to transmit torque from said handle to said distal end of the catheter shaft;

said catheter shaft and dual purpose wires together having a torsional stiffness of about 0.25 to 1.0 inch-ounce per 110 cm of length when the proximal end of the catheter shaft is rotated about 3 turns; and said catheter shaft including an axially extending dampening member.

19. A catheter according to claim 18 wherein said damping member is made of a polymer material.

20. A simplified torquing electrode catheter comprising:

a handle comprising an electrical connector;

a catheter shaft having a plurality of axial lumens, a proximal end and a distal end, the proximal end mounted to the handle;

said catheter shaft being made of a homogeneous material;

a plurality of electrodes mounted to the distal end;

a dual purpose wire secured to each of said electrodes in an electrically-conductive manner, each said dual purpose wire having an electrical resistance of no greater than about 0.80 ohms per cm;

each of said dual purpose wires secured to and extending from the handle, extending through a separate one of said axial lumens and to said electrodes so to act as electrical conductors electrically coupling the handle and the electrodes and to transmit torque from said handle to said distal end of the catheter shaft;

said catheter shaft and dual purpose wires together having a torsional stiffness of about 0.25 to 1.0 inch-ounce per 110 cm of length when the proximal end of the catheter shaft is rotated about 3 turns; and said catheter shaft including and axially extending damping member.

21. A catheter according to claim 20 wherein said damping member is made of a polymer material.

22. A simplified torquing electrode catheter comprising:

a handle;

a catheter shaft having an axial lumen, a proximal end and a distal end, the proximal end mounted to the handle;

said catheter shaft being made of a homogeneous material;

a plurality of electrodes mounted to the distal end;

a dual purpose wire secured to each of said electrodes in an electrically-conductive manner;

each of said dual purpose wires secured to and extending from the handle and through said axial lumen to said electrodes so to act as electrical conductors electrically coupling the handle and the electrodes and to transmit torque from said handle to said distal end of the catheter shaft; and wherein said catheter shaft includes an axially extending damping member.

23. An electrode catheter comprising:

a handle;

a catheter shaft having an axial lumen, a proximal end and a distal end, the proximal end mounted to the handle, the distal end having a tip;

a plurality of electrodes mounted to the distal end spaced apart from the tip;

a dual purpose wire secured to each of said electrodes in an electrically-conductive manner, each said dual purpose wire having an electrical resistance of no greater than about 0.80 ohm per cm;

said dual purpose wires secured to and extending from the handle, extending through the axial lumen in said catheter shaft and to said electrodes so to act as electrical conductors electrically coupling the handle and the electrodes and to transmit torque from said handle to said distal end of the catheter shaft; and said catheter shaft and dual purpose wires together having a torsional stiffness of about 0.25 to 1.0 inch-ounce per 110 cm of length when the proximal end of the catheter shaft is rotated about 3 turns.

24. A simplified torquing electrode catheter comprising:

a handle comprising an electrical connector;

a catheter shaft having a plurality of axial lumens, a proximal end and a distal end, the proximal end mounted to the handle, the distal end terminating in a tip;

a plurality of electrodes mounted to the distal end spaced apart from the tip;

said catheter shaft being made of a homogenous material;

a plurality of electrodes mounted to the distal end; electrodes in an electrically-conductive manner, each said dual purpose wire having an electrical resistance of no greater than about 0.80 ohms per cm to provide sufficient electrical current carrying capacity and resistivity for an electrophysiology procedure;

each of said dual purpose wires secured to and extending from the handle, extending through a separate one of said axial lumens and to said electrodes so to act as electrical conductors electrically coupling the handle and the electrodes and to transmit torque from said handle along said dual purpose wires to said distal end of the catheter shaft; and said catheter shaft and dual purpose wires together having a torsional stiffness of about 0.25 to 1.0 inch-ounce per 110 cm of length when the proximal end of the catheter shaft is rotated about 3 turns to provide a torsional stiffness sufficient to laterally deflect the distal end of the shaft by rotating the proximal end of the shaft.

* * * * *